(12) United States Patent
Inokuchi

(10) Patent No.: US 9,198,839 B2
(45) Date of Patent: Dec. 1, 2015

(54) SILICONE COMPOSITE PARTICLE AND A METHOD FOR PREPARING THE SAME

(71) Applicant: SHIN-ETSU CHEMICAL CO., LTD., Tokyo (JP)

(72) Inventor: Yoshinori Inokuchi, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/253,257

(22) Filed: Apr. 15, 2014

(65) Prior Publication Data
US 2014/0322280 A1    Oct. 30, 2014

(51) Int. Cl.
| | | |
|---|---|---|
| *A61K 9/50* | (2006.01) | |
| *A61K 8/02* | (2006.01) | |
| *B01J 13/02* | (2006.01) | |
| *C08L 83/04* | (2006.01) | |
| *A61K 8/81* | (2006.01) | |
| *A61Q 1/00* | (2006.01) | |
| *A61K 8/31* | (2006.01) | |
| *A61Q 1/02* | (2006.01) | |
| *A61K 8/891* | (2006.01) | |
| *A61K 8/895* | (2006.01) | |

(52) U.S. Cl.
CPC ............ *A61K 8/0245* (2013.01); *A61K 8/0283* (2013.01); *A61K 8/31* (2013.01); *A61K 8/8194* (2013.01); *A61K 8/891* (2013.01); *A61K 8/895* (2013.01); *A61Q 1/00* (2013.01); *A61Q 1/02* (2013.01); *B01J 13/02* (2013.01); *C08L 83/04* (2013.01); *A61K 2800/412* (2013.01); *A61K 2800/413* (2013.01); *A61K 2800/594* (2013.01); *A61K 2800/614* (2013.01); *A61K 2800/624* (2013.01); *A61K 2800/654* (2013.01)

(58) Field of Classification Search
CPC ....................................................... B01J 13/02
See application file for complete search history.

(56) References Cited

U.S. PATENT DOCUMENTS

| | | | |
|---|---|---|---|
| 4,892,726 A | 1/1990 | Yonekura et al. | |
| 8,133,586 B2 * | 3/2012 | Inokuchi et al. | 428/403 |

(Continued)

FOREIGN PATENT DOCUMENTS

| | | |
|---|---|---|
| JP | A-63-297313 | 12/1988 |
| JP | A-8-12524 | 1/1996 |

(Continued)

*Primary Examiner* — Carlos Azpuru
(74) *Attorney, Agent, or Firm* — Oliff PLC

(57) ABSTRACT

The purpose of the present invention is to provide a silicone rubber particle having a higher light scattering property which can be expected to provide makeup cosmetics such as a foundation with a higher soft focus effect, and a method for preparing the same. The present invention provides a silicone composite particle composed of a silicone rubber particle and a polyorganosilsesquioxane, wherein the silicone rubber particle has plural dents on its surface and said polyorganosilsesquioxane adheres to the surface of the silicone rubber particle. Further, the present invention provides a method for preparing the silicone composite particle, wherein the method includes steps of subjecting organotrialkoxysilane to a hydrolysis and subsequent condensation in the presence of water, an alkaline substance and a silicone rubber particle containing therein a liquid to thereby have a resultant polyorganosilsesquioxane adhered to the surface of the silicone rubber particle, and subsequently removing the liquid.

3 Claims, 3 Drawing Sheets

(56) References Cited

U.S. PATENT DOCUMENTS

| | | | |
|---|---|---|---|
| 8,632,791 B2* | 1/2014 | Inokuchi et al. | 424/401 |
| 8,703,163 B2* | 4/2014 | Inokuchi et al. | 424/401 |
| 2011/0129672 A1 | 6/2011 | Aratani et al. | |
| 2011/0142893 A1 | 6/2011 | Ishikawa et al. | |
| 2011/0171157 A1 | 7/2011 | Aratani et al. | |
| 2011/0224308 A1 | 9/2011 | Saito et al. | |

FOREIGN PATENT DOCUMENTS

| | | |
|---|---|---|
| JP | A-9-20631 | 1/1997 |
| JP | A-2000-191788 | 7/2000 |
| JP | A-2004-359592 | 12/2004 |
| JP | A-2011-1537 | 1/2011 |
| JP | A-2011-57785 | 3/2011 |
| WO | WO 2011/074066 A1 | 6/2011 |
| WO | WO 2011/111179 A1 | 9/2011 |

* cited by examiner

SILICONE COMPOSITE PARTICLE AND A METHOD FOR PREPARING THE SAME

CROSS REFERENCE

This application claims the benefits of Japanese Patent application No. 2013-094146 filed on Apr. 26, 2013, the contents of which are incorporated by reference.

The present invention relates to a silicone composite particle and a method for preparing the same.

BACKGROUND OF THE INVENTION

Various spherical silicone particles have been used in order to provide a non-sticky or smooth feeling or extensibility to cosmetics. For instance, Japanese Patent Application Laid-Open No. Sho63-297313 describes cosmetics containing polymethylsilsesquioxane powder, Japanese Patent Application Laid-Open No. H08-12524 describes makeup cosmetics containing spherical silicone rubber powder and Japanese Patent Application Laid-Open No. H09-20631 describes cosmetics containing composite silicone powder composed of spherical silicone rubber microparticles covered with a polyorganosilsesquioxane resin. These silicone rubber particles and the particle composed of spherical silicone rubber microparticles covered with a polyorganosilsesquioxane resin provide a soft feeling, in addition to the aforesaid feeling, to cosmetics.

Makeup cosmetics such as a foundation, containing silicone particles provide an effect of natural finish without artificial gloss, i.e. soft focus effect, to cosmetics. For instance, in the cosmetics obtained in the method described in Japanese Patent Application Laid-Open No. H09-2063, the polyorganosilsesquioxane covering the silicone particles has a particle diameter of approximately 100 nm. The polyorganosilsesquioxane also scatters light to provide a high soft focus effect to cosmetics.

Further, it is known to provide many convexes or concaves on a surface of silicone particles or making a shape of silicone particles non-spherical to improve a light scattering property. Japanese Patent Application Laid-Open No. 2004-359592 describes spherical polyorganosilsesquioxane particles having a projection on its surface. Japanese Patent Application Laid-Open No. 2000-191788 describes spherical organosilicone microparticles having many dents on its surface. Japanese Patent Application Laid-Open No. 2011-1537 describes organosilicone microparticles having a hollow spindle shape with plural concaves on its surface. Japanese Patent Application Laid-Open No. 2011-57785 describes deformed organosilicone microparticles having a hexahedron or polyhedron shape with each face being concave. WO 2011/074066 describes organosilicone microparticles which are spherical as a whole, and have, on its surface, plural indefinite faces and a protruded network structure surrounding the indefinite faces. WO 2011/111179 describes organosilicone microparticles which are tetrahedral as a whole and have concaves with a generally circular periphery on each face of the tetrahedron.

PRIOR LITERATURES

Patent Literatures

[Patent Literature 1] Japanese Patent Application Laid-Open No. Sho63-297313
[Patent Literature 2] Japanese Patent Application Laid-Open No. H08-12524
[Patent Literature 3] Japanese Patent Application Laid-Open No. H09-20631
[Patent Literature 4] Japanese Patent Application Laid-Open No. 2004-359592
[Patent Literature 5] Japanese Patent Application Laid-Open No. 2000-191788
[Patent Literature 6] Japanese Patent Application Laid-Open No. 2011-1537
[Patent Literature 7] Japanese Patent Application Laid-Open No. 2011-57785
[Patent Literature 8] WO 2011/074066
[Patent Literature 9] WO 2011/111179

SUMMARY OF THE INVENTION

However, the aforesaid polyorganosilsesquioxane particles and organic silicone microparticles are resinous hard materials and, therefore, cannot provide soft feeling to cosmetics. In recent years, it is becoming important that makeup cosmetics such as foundations provide inartificial natural finish, i.e. bare skin-like feeling. Therefore, it is desired to provide a higher light scattering effect by silicone rubber particles.

One of the purposes of the present invention is to provide a silicone rubber particle having a higher light scattering property which particle is expected to provide makeup cosmetics such as foundations with a higher soft focus effect, and a method for preparing the same.

The present inventors have made research and found a novel silicone composite particle composed of a silicone rubber particle having plural dents on its surface and a polyorganosilsesquioxane which adheres to the surface of the silicone rubber particle, and a method for preparing the same.

Thus, the present invention provides a silicone composite particle composed of a silicone rubber particle and a polyorganosilsesquioxane, wherein the silicone rubber particle has plural dents on its surface and said polyorganosilsesquioxane adheres to the surface of the silicone rubber particle.

Further, the present invention provides a method for preparing the silicone composite particle comprising steps of subjecting organotrialkoxysilane to hydrolysis and condensation reactions in the presence of water, an alkaline substance, and a silicone rubber particle containing therein a liquid to thereby have a resultant polyorganosilsesquioxane adhered to the surface of the silicone rubber particle, and subsequently removing the liquid.

The present silicone composite particle is expected to have a higher light scattering effect.

DETAILED DESCRIPTION OF THE INVENTION

Figure 1:
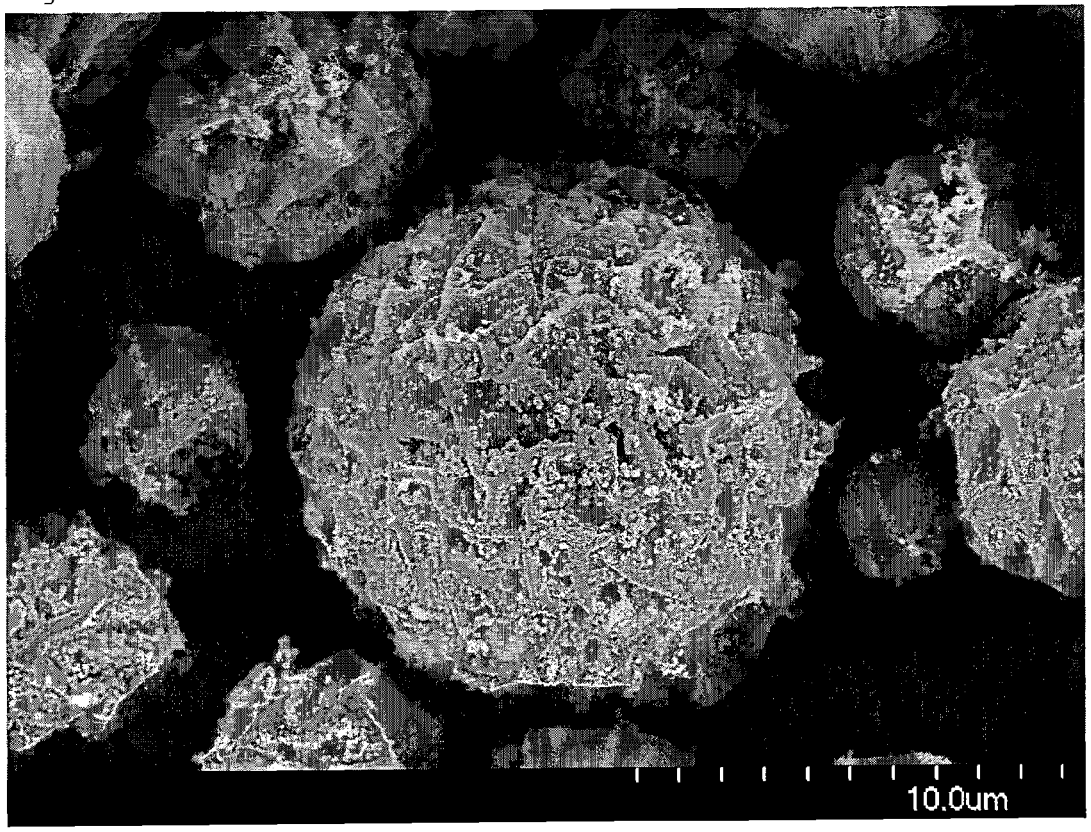
FIG. 1 is an electron microscope image of a surface of the silicone composite particle obtained in Example 1.

The present invention will be described below in detail.
[Silicone Composite Particle]
The present invention provides a silicone composite particle composed of a silicone rubber particle and polyorganosilsesquioxane. The present invention is characteristic in that the silicone rubber particle has plural dents on its surface and the polyorganosilsesquioxane adheres to the surface of the silicone rubber particle.

Silicone Rubber Particle

The silicone rubber particle preferably has a volume-average particle diameter of 0.5 to 100 µm, more preferably 1 to 40 µm. If the volume-average particle diameter is less than the aforesaid lower limit, the silicone composite particles obtained have a higher tendency for agglomeration. It is not easy to disperse the agglomerated particles into primary particles. Further, the agglomerated particles give cosmetics a less non-sticky feeling. If the volume-average particle diameter is larger than the aforesaid upper limit, non-sticky feeling and smoothness of cosmetics decrease and rough feeling appears. A method for determining the volume-average particle diameter is selected depending on a particle diameter of the silicone composite particle. When the particle diameter is 1 µm or more, an electric resistance method is used. When the particle diameter is less than 1 µm, a laser diffraction-scattering method is used.

The silicone rubber particle has plural dents on its surface. The shape of the dent may be any of a part of spherical surface and a polyhedron. In the present method described below, polyhedral dents are mostly formed, rather than dents of a part of spherical surface. The polyhedron here may be a convex polyhedron whose all interior angles are less than 180 degrees or a concave polyhedron whose at least one interior angle is larger than 180 degrees. The number of the dents is at least two, preferably three or more, per silicone rubber particle. If the number of dents is less than two, a high light scattering effect is not expected. The upper limit of the number of the dents is not limited to any particular one, but generally depends on a size of the silicone rubber particle and a longest diameter of the dent. The longest diameter of the dent is preferably 100 nm or more, more preferably 200 nm or more. If the longest diameter is shorter than 100 nm, a higher light scattering effect is not expected. The upper limit of the longest diameter depends on a surface area of the silicone rubber particle, but is not limited to any particular one. When the silicone rubber particle has more dents on its surface, the longest diameter of the dent tends to be shorter and the shape of the silicone rubber particle is nearly spherical. When the silicone rubber particle has a fewer dents on its surface, the longest diameter of the dent tend to be longer and the silicone rubber particle is mostly of a indefinite shape. The shape of the present silicone rubber particle can be confirmed by observation with an optical microscope or an electron microscope. The shape, the number and the longest diameter of the dents on the particle surface can be confirmed by observation with an electron microscope.

The silicone rubber which constitutes the silicone rubber particle is preferably non-sticky and has a rubber hardness of 5 to 35, more preferably 10 to 30, as determined with a Type A durometer in accordance with the Japanese Industrial Standards (JIS) K 6253. If the rubber hardness is less than the aforesaid lower limit, the silicone composite particles obtained has a tendency for agglomeration and do not easily disperse to become primary particles and, further, a non-sticky feeling of cosmetics decreases. If the rubber hardness is larger than the aforesaid upper limit, a silicone composite particle having dents cannot be obtained in the present method described below.

The silicone rubber is particularly a cured product having a linear organosiloxane block represented by the formula —($R^1_2SiO_{2/2}$)$_n$—, wherein $R^1$ is an unsubstituted or substituted monovalent hydrocarbon group having 1 to 30 carbon atoms and n is a positive integer of from 5 to 5,000.

Examples of $R^1$ include an alkyl group such as a methyl group, an ethyl group, a propyl group, a butyl group, a pentyl group, a hexyl group, a heptyl group, an octyl group, a decyl group, an undecyl group, a dodecyl group, a tetradecyl group, a pentadecyl group, a hexadecyl group, a heptadecyl group, an octadecyl group, a nonadecyl group, an eicosyl group, a henicosyl group, a docosyl group, a tricosyl group, a tetracyl group, and a triacontyl group; an aryl group such as a phenyl group, a tolyl group, and a naphthyl group; an aralkyl group such as a benzyl group and a phenethyl group; an alkenyl group such as a vinyl group and an allyl group; a cycloalkyl group such as a cyclopentyl group, a cyclohexyl group, and a cycloheptyl group; and those hydrocarbon groups wherein a part or all of the hydrogen atoms bonded to a carbon atom of these groups is substituted with a substituent as a halogen atom such as a fluorine atom, a chlorine atom, a bromine atom and an iodine atom and/or an amino group, an acryloyloxy group, a methacryloyloxy group, an epoxy group, glycidoxy group, a mercapto group and a carboxyl group.

The silicone rubber particle is obtained by curing a curable liquid silicone composition, for instance, by a condensation reaction of a compound having a methoxy silyl group (≡SiOCH$_3$) and a compound having a hydroxy silyl group (≡SiOH), a radical reaction of a compound having a mercaptopropyl silyl group (≡Si—C$_3$H$_6$SH) and a compound having a vinyl silyl group (≡SiCH=CH$_2$), or an addition reaction of a compound having a vinyl silyl group (≡SiCH=CH$_2$) and a compound having a hydrosilyl group (≡SiH). Among these reactions, the addition reaction is preferable in view of reactivity.

In a case where the silicone rubber particle is prepared by the addition reaction, a liquid silicone composition comprising a combination of an organopolysiloxane having monovalent olefinic unsaturated groups and an organohydrogen polysiloxane may be subjected to an addition reaction in the presence of a platinum group metal catalyst, wherein the organopolysiloxane is represented by an average formula: $R^2_aR^3_bSiO_{(4-a-b)/2}$ and having at least two monovalent olefinic unsaturated groups per molecule and the organohydrogen polysiloxane is represented by an average formula: $R^4_cH_dSiO_{(4-c-d)/2}$ and having at least three hydrogen atoms each bonded to a silicone atom per molecule; or the organopolysiloxane is represented by an average formula: $R^2_aR^3_bSiO_{(4-a-b)/2}$ and having at least three monovalent olefinic unsaturated groups per molecule and the organohydrogen polysiloxane is represented by an average formula: $R^4_cH_dSiO_{(4-c-d)/2}$ and having at least two hydrogen atoms each bonded to a silicon atom per molecule; wherein a ratio of the organopolysiloxane having monovalent olefinic unsaturated groups to the organohydrogen polysiloxane is such that the number of the hydrosilyl group is 0.5 to 2, per the number of the monovalent olefinic unsaturated group.

In the aforesaid formula, $R^2$ is an unsubstituted or substituted monovalent hydrocarbon group having 1 to 30 carbon atoms but is not an aliphatic unsaturated group. $R^3$ is a monovalent olefinic unsaturated group, for instance, an alkenyl group having 2 to 6 carbon atoms. "a" and "b" are positive numbers satisfying the equations, 0<a<3, 0<b<=3 and 0.1<=a+b<=3, preferably 0<a<=2.295, 0.005<=b<=2.3 and 0.5<=a+b<=2.3. $R^4$ is an unsubstituted or substituted monovalent hydrocarbon group having 1 to 30 carbon atoms but is not an aliphatic unsaturated group. "c" and "d" are positive numbers satisfying the equations, 0<c<3, 0<d<=3 and 0.1<=c+d<=3, preferably 0<c<=2.295, 0.005<=d<=2.3 and 0.5<=c+d<=2.3.

Examples of $R^2$ include an alkyl group such as a methyl group, an ethyl group, a propyl group, a butyl group, a pentyl group, a hexyl group, a heptyl group, an octyl group, a decyl group, an undecyl group, a dodecyl group, a tetradecyl group, a pentadecyl group, a hexadecyl group, a heptadecyl group, an octadecyl group, a nonadecyl group, an eicosyl group, a henicosyl group, a docosyl group, a tricosyl group, a tetracyl group and a triacontyl group; an aryl group such as a phenyl group, a tolyl group and a naphthyl group; an aralkyl group such as a benzyl group and a phenethyl group; a cycloalkyl group such as a cyclopentyl group, a cyclohexyl group and a cycloheptyl group; and those hydrocarbon groups wherein a part or all of the hydrogen atoms bonded to a carbon atom of these groups is substituted with a substituent such as a halogen atom such as a fluorine atom, a chlorine atom, a bromine atom and an iodine atom and/or an amino group, an acryloyloxy group, a methacryloyloxy group, an epoxy group, a glycidoxy group and a carboxyl group. Particularly, it is industrially preferable that 50 mole % or more of $R^2$ are a methyl group.

Examples of $R^3$ include a vinyl group, an allyl group, a propenyl group, a butenyl group, a pentenyl group and a hexenyl group. Particularly, a vinyl group is industrially preferable.

Examples of $R^4$ include the same groups as those described above for $R^2$.

The organopolysiloxane and the organohydrogenpolysiloxane preferably have a viscosity at 25 degrees C. of 100,000 mm$^2$/s or less, more preferably 10,000 mm$^2$/s or less. If the viscosity is higher than the aforesaid upper limit, it is difficult to obtain a particle having a narrow molecular weight range in the present method described below. The organopolysiloxane and the organohydrogenpolysiloxane may be a linear, cyclic or branched structure. Particularly, a linear structure is preferable. The viscosity in the present invention is determined at 25 degrees C. with an Ostwald viscometer.

For preparing the present silicone rubber particle, it is preferable, as mentioned above, that the liquid curable silicone composition comprises a combination of an organopolysiloxane having at least two monovalent olefinic unsaturated groups per molecule and an organohydrogenpolysiloxane having at least three hydrogen atoms each bonded to a silicon atom per molecule, or a combination of an organopolysiloxane having at least three monovalent olefinic unsaturated groups per molecule and an organohydrogenpolysiloxane having at least two hydrogen atoms each bonded to a silicon atom per molecule. If the combination of the polysiloxanes is not as mentioned above, a cured rubber tends to be sticky.

The platinum group metal catalyst may be a well-known or known catalyst for hydrosilylation. Examples of the catalyst include an element of platinum group metals such as platinum, including platinum black, rhodium and palladium; platinum chloride such as $H_2PtCl_4 \cdot kH_2O$, $H_2PtCl_6 \cdot kH_2O$, $NaHPtCl_6 \cdot kH_2O$, $KHPtCl_6 \cdot kH_2O$, $Na_2PtCl_6 \cdot kH_2O$, $K_2PtCl_4 \cdot kH_2O$, $PtCl_4 \cdot kH_2O$, $PtCl_2$, and $Na_2HPtCl_4 \cdot kH_2O$, wherein "k" is an integer of 0 to 6, preferably 0 or 6; a chloroplatinic acid and a chloroplatinate; an alcohol-modified chloroplatinic acid (see U.S. Pat. No. 3,220,972); a complex of chloroplatinic acid with an olefin (see U.S. Pat. No. 3,159,601, U.S. Pat. No. 3,159,662, and U.S. Pat. No. 3,775,452); a platinum group metal, such as platinum black and palladium, supported on a carrier such as alumina, silica and carbon; a rhodium-olefin complex; chlorotris(triphenylphosphine) rhodium (Wilkinson catalyst); and a complex of platinum chloride, chloroplatinic acid or chloroplatinate with siloxane having a vinyl group, in particular vinyl group-containing cyclic siloxane.

The amount of the platinum group metal catalyst may be an effective amount as a hydrosilylation catalyst. The amount of the catalyst is usually such that the amount of the platinum group metal in the catalyst is about 0.1 to about 500 ppm by mass, preferably about 0.5 to about 200 ppm by mass, more preferably about 1 to about 100 ppm by mass, relative to a total mass of the curable liquid silicone composition.

The silicone rubber particle may contain a silicone oil, inorganic powder and organic powder.

Polyorganosilsesquioxane

In the present invention, the polyorganosilsesquioxane is preferably particulate. The particle diameter is 10 to 400 nm, preferably 50 to 200 nm. If the particle diameter is smaller than the aforesaid lower limit, the light scattering effect of the silicone composite particle tends to decrease. If the particle diameter is larger than the aforesaid upper limit, soft feeling of cosmetics and a light scattering effect of the silicone composite particle tend to decrease. Further, if the particle diameter is too large, there is a tendency that dents are not formed on the surface of the particle. The particle diameter of the polyorganosilsesquioxane should be smaller than that of the aforesaid silicone rubber particle. The polyorganosilsesquiocane particles may attach to the surface of the silicone rubber particle in a scattered state or in a dense state. Higher dense state is preferable because many dents are easily formed. The shape of the polyorganosilsesquioxane particles is not limited, but preferably almost spherical or hemispherical. The diameter and shape of the polyorganosilsesquioxane particles and density on the particle surface may be confirmed by observing the silicone composite particle with an electron microscope.

The amount of the polyorganosilsesquioxane adhered on the surface of the silicone rubber particle is preferably 1 to 50 parts by mass, more preferably 2 to 25 parts by mass, per 100 parts by mass of the silicone rubber particles. If the amount is smaller than the aforesaid lower limit, the light scattering effect of the silicone composite particles and the non-sticky feeling of cosmetics decrease and, further, there is a tendency that dents are not formed on the surface of the silicone rubber particle. If the amount is larger than the aforesaid upper limit, a soft feeling of cosmetics decreases.

The polyorganosilsesquioxane is a resinous solid composed of three-dimensionally crosslinked units represented by, for instance, a formula, $R^5SiO_{3/2}$, to form a network, wherein $R^5$ is an unsubstituted or substituted monovalent hydrocarbon group having 1 to 20 carbon atoms. Examples of $R^5$ include an alkyl group such as a methyl group, an ethyl group, a propyl group, a butyl group, a pentyl group, a hexyl group, a heptyl group, an octyl group, a decyl group, a undecyl group, a dodecyl group, a tetradecyl group, a pentadecyl group, a hexadecyl group, a heptadecyl group, an octadecyl group, a nonadecyl group and an eicosyl group; an alkenyl group such as a vinyl group and an allyl group; an aryl group such as a phenyl group, a tolyl group and a naphthyl group; an aralkyl group such as a benzyl group and a phenethyl group; a cycloalkyl group such as a cyclopentyl group, a cyclohexyl group and a cycloheptyl group; and those hydrocarbon groups wherein a part or all of the hydrogen atoms bonded to a carbon atom of these groups is substituted with a substituent such as a halogen atom such as a fluorine atom, a chlorine atom, a bromine atom and an iodine atom and/or an amino group, an acryloyloxy group, a methacryloyloxy group, an epoxy group, a glycidoxy group, a mercapto group, and a carboxyl group. For the polyorganosilsesquioxane to adhere to the surface of the silicone rubber particle, 50 mole % or more, more preferably 80 mole % or more, further preferably 90 mole % or more, of $R^5$ is preferably a methyl group, a vinyl group or a phenyl group.

The polyorganosilsesquioxane may contain, in addition to $R^5SiO_{3/2}$ unit, one or more units represented by $R^5_2SiO_{2/2}$, $R^5_3SiO_{1/2}$ or $SiO_{4/2}$, as long as non-aggregability and dispersibility of the silicone composite particle and feeling such as non-sticky, smooth and soft feeling of cosmetics are not lost. In this polyorganosilsesquioxane, the amount of the $R^5SiO_{3/2}$ unit is preferably 70 to 100 mole %, more preferably 80 to 100 mole %, relative to the whole siloxane units.

[Preparation of a Silicone Composite Particle]

The present invention further provides a method for preparing the afore-mentioned silicone composite particle. The present method comprises a step (i): an organotrialkoxysilane is subjected to hydrolysis and condensation reactions in the presence of water, an alkaline substance and a silicone rubber particle containing therein a liquid; and a step (ii): the liquid is subsequently removed. Until the step of adhering polyorganosilsesquioxane on the surface of the silicone rubber particle, i.e. the aforesaid step (i), the silicone composite particle have no dent on its surface. In the step of removing the liquid, i.e. the aforesaid step (ii), the silicone rubber particle shrinks and, thereby, dents appear on the surface.

The present method will be described below in detail.

(0) Preparation of a Silicone Rubber Spherical Particle Containing a Liquid

The silicone rubber spherical particle containing a liquid may be prepared according to any conventional manners. For instance, it can be prepared in a state of an aqueous dispersion of the silicone rubber particle containing silicone oil. The aqueous dispersion may be prepared, for instance, in a manner where an intended liquid is dissolved in the aforesaid curable liquid silicone composition, to which a surfactant and water are added, emulsified to prepare an emulsion, subsequently a catalyst is added thereto and, then, a curing reaction is conducted. The present method may comprise a step of having a liquid contained to a silicone rubber particle, before the aforesaid step (i).

The liquid to be contained in the silicone rubber particle needs to be soluble in the curable liquid silicone composition and to be unreactive with the curable liquid silicone composition. The liquid is not particularly limited as long as it meets the aforesaid requirements. The liquid preferably has a boiling point of 30 to 500 degrees C., more preferably 50 to 300 degrees C. When the boiling point is lower the aforesaid upper limit, the liquid can be removed only by evaporation, so that process steps are fewer and an amount of the liquid remaining in the silicone composite particle is less.

Examples of the liquid to be contained in the silicone rubber particle include aliphatic hydrocarbons such as pentane, hexane, heptane, octane, nonane, decane, undecane, dodecane, hexadecane, octadecane, cyclohexane; aromatic hydrocarbons such as benzene, toluene, ethylbenzene and xylene; alcohols such as butanol, hexanol, octanol, decanol, cyclohexanol and benzylalcohol; halogenated hydrocarbons such as chloroform, carbon tetrachloride, ethyl chloride and chlorobenzene; esters such as ethyl acetate, isopropyl acetate, ethyl acetoacetate, amil acetate, isobutyl isobytyrate and benzyl acetate; ethers such as ethyl ether, butyl ether, tetrahydrofuran and 1,4-dioxane; ketones such as acetone, methyl ethyl ketone, cyclohexanone, diaceton alcohol, methyl amyl ketone and diisobutyl ketone.

The liquid may be an organopolysiloxane. Such an organopolysiloxane is represented by an average formula: $R^6_e SiO_{(4-e)/2}$. $R^6$ is an unsubstituted or substituted monovalent hydrocarbon group having 1 to 30 carbon atoms and e is a positive number satisfying $1<=e<=3$, preferably $0.5<=e<=2.3$. Examples of $R^6$ include an alkyl group such as a methyl group, an ethyl group, a propyl group, a butyl group, a pentyl group, a hexyl group, a heptyl group, an octyl group, a decyl group, a undecyl group, a dodecyl group, a tetradecyl group, a pentadecyl group, a hexadecyl group, a heptadecyl group, an octadecyl group, a nonadecyl group, an eicosyl group, a henicosyl group, a docosyl group, a tricosyl group, a tetracosyl group and a triacontyl group; an aryl group such as a phenyl group, a tolyl group, and a naphthyl group; an aralkyl group such as a benzyl group and a phenethyl group; an alkenyl group such as a vinyl group and an allyl group; a cycloalkyl group such as a cyclopentyl group, a cyclohexyl group and a cycloheptyl group; and those hydrocarbon groups wherein a part or all of the hydrogen atoms bonded to a carbon atom of these groups is substituted with a substituent such as a halogen atom; fluorine atom, chlorine atom, bromine atom, and iodine atom and/or an amino group, an acryloyloxy group, a methacryloyloxy group, an epoxy group, a glycidoxy group, a mercapto group and a carboxyl group. It is industrially preferable that 50 mole % or more of $R^6$ are a methyl group. This organopolysiloxane preferably has a viscosity at 25 degrees C. of 100,000 $mm^2/s$ or less, more preferably 10,000 $mm^2/s$ or less. If the viscosity is higher than the aforesaid upper limit, it is difficult to prepare particles with a narrow size distribution in the present method. The organopolysiloxane may be linear, cyclic or branched. The aforesaid viscosity is determined at 25 degrees C. with an Ostwald viscometer.

The liquid to be contained in the silicone rubber particle may be one or a combination of two or more of the aforesaid liquids. The amount of the liquid is preferably 5 to 80 parts by mass, more preferably 10 to 70 parts by mass, per 100 parts by mass of the curable liquid silicone composition containing a liquid. That is, the amount of the liquid is preferably 5 to 80 parts by mass, more preferably 10 to 70 parts by mass, per 100 parts by mass of the silicone rubber particle containing the liquid. If the amount of the liquid is smaller than the aforesaid lower limit, no dent is formed on the surface of the silicone rubber particle after removing the liquid. If the amount of the liquid is larger than the aforesaid upper limit, the rubber hardness of the silicone rubber particle is lower, and silicone composite particles obtained have a higher tendency for agglomeration, so that they are not easily dispersed into primary particles and, further, a non-sticky feeling of cosmetics decreases.

The surfactant is used as an emulsifier in order to emulsify the curable liquid silicone composition containing the aforementioned liquid in water. The surfactant is not limited to any particular one and may be a nonionic surfactant, an anionic surfactant, a cationic surfactant and an amphoteric surfactant.

Examples of the nonionic surfactant include a polyoxyethylene alkyl ether, a polyoxyethylene polyoxypropylene alkyl ether, a polyoxyethylene alkyl phenyl ether, a polyethylene glycol fatty acid ester, a sorbitan fatty acid ester, a polyoxyethylene sorbitan fatty acid ester, a polyoxyethylene sorbit fatty acid ester, a glycerin fatty acid ester, a polyoxyethylene glycerin fatty acid ester, a polyglycerin fatty acid ester, a propylene glycol fatty acid ester, a polyoxyethylene castor oil, a polyoxyethylene cured castor oil, a polyoxyethylene cured castor oil fatty acid ester, a polyoxyethylene alkyl amine, a polyoxyethylene fatty acid amide, an organopolysiloxane modified with polyoxyethylene, and an organopolysiloxane modified with polyoxyethylene polyoxypropylene.

Examples of the anionic surfactant include alkyl sulfate ester salt, polyoxyethylene alkylether sulfate ester salt, polyoxyethylene alkylphenyl ether sulfate ester salt, sulfate ester salt of aliphatic acid alkylol amide, alkyl benzene sulfur acid salt, polyoxyethylene alkylphenyl ether sulfur acid salt, alpha-olefin sulfur acid salt, alpha-sulfo aliphatic acid ester salt, alkylnaphthalene sulfur acid salt, alkyldiphenylether disulfur acid salt, alkane sulfur acid, N-acyl taurine acid salt, dialkylsulfosuccinic acid salt, monoalkylsulfosuccinic acid salt, polyoxyethylene alkyl ether sulfosuccinic acid salt, aliphatic acid salt, polyoxyethylene alkyl ether carboxylic acid salt, N-acylamino acid salt, monoalkyl phosphoric acid ester salt, dialkyl phosphoric acid ester salt and polyoxyethylene alkylether phosphoric acid ester salt.

Examples of the cationic surfactant include an alkyl trimethyl ammonium salt, a dialkyl dimethyl ammonium salt, a polyoxyethylene alkyl dimethyl ammonium salt, a dipolyoxyethylene alkyl methyl ammonium salt, a tripolyoxyethylene alkyl ammonium salt, an alkyl benzyl dimethyl ammonium salt, an alkyl pyridinium salt, a monoalkyl amine salt and a monoalkylamide amine salt.

Examples of the amphoteric surfactant include an alkyl dimethyl amine oxide, an alkyl dimethyl carboxybetaine, an alkylamide propyl dimethyl carboxybetaine, an alkyl hydroxysulfobetaine and an alkyl carboxymethyl hydroxyethyl imidazolinium betaine.

These surfactants may be used singly or as a mixture of two or more. In particular, a nonionic surfactant is preferable because even a small amount of it can emulsify the aforesaid liquid silicone composition into fine particles. The amount of the surfactant is preferably 0.01 to 20 parts by mass, more preferably 0.05 to 5 parts by mass, per 100 parts by mass of the curable liquid silicone composition containing the aforesaid liquid. If the amount of the surfactant is too large, polyorganosilsesquioxane may not adhere to the surface of the silicone rubber particle in the present preparation method. If the amount of the surfactant is less than the lower limit, it is difficult to obtain a fine particle.

The emulsification may be conducted with a conventional emulsification and dispersion apparatus. Examples of the emulsification and dispersion apparatus include a high-speed rotation and centrifugal emission type agitator such as a homodisper; a high-speed rotation and shearing type agitator such as a homomixer; a high-pressure injection-type emulsification disperser such as a homogenizer; a colloid mill; and an ultrasonic emulsifier.

The silicone rubber particle containing a liquid can be prepared by adding a catalyst to the emulsion obtained in the afore-mentioned emulsification, followed by curing. The catalyst may be the afore-mentioned platinum group metal catalyst when the curable liquid silicone composition is of an addition reaction type. When the dispersibility of the catalyst in water is poor, it is preferable that the catalyst is dissolved in a surfactant and added to the emulsion. The surfactant may be those as described above. In particular, a nonionic surfactant is preferable. The curing reaction may be conducted at room temperature. If the reaction is not complete, the curing may be conducted under heating at a temperature below 100 degrees C.

The catalyst may be added in the curable liquid silicone composition in advance. In this case, it is better to take into consideration a reactivity of the curing liquid silicone composition and a reaction temperature and time so as not to cause curing before finishing the step of the emulsification. Additionally, a reaction retardant may be added in the curing liquid silicone composition.

According to the afore-mentioned method, an aqueous dispersion of a silicone rubber particle containing a liquid is obtained. This aqueous dispersion as such may be use in the subsequent step (i). If necessary, water may be further added to the aqueous dispersion. The amount of silicone rubber particles containing a liquid is preferably 1 to 150 parts by mass, more preferably 5 to 70 parts by mass, per 100 parts by mass of water. If the amount is smaller than the lower limit, the yield of the intended silicone composite particles tends to be poor. If the amount is larger than the upper limit, the polyorganosilsesquioxane resin may not adhere to the surface of the silicone rubber particle and, also, aggregation and agglomeration of the particles tend to occur.

Further, a surfactant or a water-soluble polymer may be added to the aforesaid aqueous dispersion in order to control an adhesion property of the polyorganosilsesquioxane to the surface of the silicone rubber particle and a size of the composite particle to be obtained.

The surfactant further added to the aqueous dispersion may be the afore-mentioned surfactant, but is not limited to particular one. The surfactant may be same as or different from the surfactant contained in the aqueous dispersion of the silicone rubber particles. Two or more kinds of the surfactants may be added.

The water-soluble polymer may be a nonionic water-soluble polymer, an anionic water-soluble polymer, a cationic water-soluble polymer and an amphoteric water-soluble polymer, but is not limited to these. These aqueous polymers may be used singly, or in combination of two or more of them.

Examples of the nonionic water-soluble polymer include a copolymer of vinylalcohol and vinyl acetate, a polymer of acrylamide, a polymer of vinyl pyrrolidone, a copolymer of vinyl pyrrolidone and vinyl acetate, polyethyleneglycol, a polymer of isopropylacrylamide, a polymer of methyl vinyl ether, starch, methyl cellulose, hydroxyethyl cellulose, hydroxypropyl cellulose, guar gum and xanthan gum.

Examples of the anionic water-soluble polymer include a polymer of sodium acrylate, a copolymer of sodium acrylate and sodium maleate, a copolymer of sodium acrylate and acrylamide, a polymer of styrenesulfonic acid sodium, a copolymer of polyisoprene sulfonic acid sodium and styrene, a polymer of sodium naphthalenesulfonate, carboxymethylstarch, starch phosphate, carboxymethyl cellulose, sodium alginate, gum arabic, carrageenan, sodium chondroitin sulfate and sodium hyaluronate.

Example of the cationic water-soluble polymer include a polymer of dimethyl diallyl ammonium chloride, a polymer of vinyl imidazoline, a polymer of methyl vinyl imidazolium chloride, a polymer of ethyl acrylate trimethyl ammonium chloride, a polymer of ethyl methacrylate trimethyl ammonium chloride, a polymer of (3-acrylamidopropyl)trimethylammonium chloride, a polymer of (3-methacrylamidepropyl)trimethylammonium chloride, a copolymer of epichlorohydrin and dimethylamine, a polymer of ethylene imine, a quaternary compound of polyethylene imine, a polymer of allylamine hydrochloride salt, polylysine, cationic starch, cationic cellulose, chitosan, and these substances copolymerized with a monomer containing a nonionic group or an anionic group.

Examples of the amphoteric water-soluble polymer include a copolymer of ethyl acrylate trimethyl ammonium chloride, acrylic acid and acrylamide; a copolymer of ethyl methacrylate trimethyl ammonium chloride, acrylic acid and acrylamide; and Hofmann degradation product of a polymer of acrylamide.

(i) Step of Having a Polyorganosilsesquioxane Adhered on the Particle Surface

The present method comprises steps of subjecting organotrialkoxysilane to hydrolysis and subsequent condensation in the presence of water, an alkaline substance and a silicone rubber particle containing a liquid to thereby have a resultant polyorganosilsesquioxane adhered on the surface of the silicone rubber particles. The alkaline substance works as a catalyst for hydrolysis and condensation reactions of the organotrialkoxysilane. The alkaline substance may be used singly, or two or more of them. The alkaline substance may be added as it is or as an aqueous alkaline solution. The alkaline substance may be added before or after the organotrialkoxysilane is added to an aqueous dispersion of water and silicone rubber particles containing a liquid.

The amount of the alkaline substance is such that a pH of the aqueous dispersion of water and the silicone rubber particle containing a liquid is preferably in the range of 9.0 to 13.0, more preferably 9.5 to 12.5. When the pH is in the aforesaid range, the hydrolysis and condensation reaction of organotrialkoxy silane proceeds sufficiently to thereby have a resultant polyorganosilsesquioxane adhered sufficiently to the surface of the silicone rubber particle.

Any alkaline substance can be use, as long as it promotes the hydrolysis and condensation reactions of organotrialkoxy silane. Examples of the alkaline substance include alkaline metal hydroxide such as potassium hydroxide, sodium hydroxide, and lithium hydroxide; an alkaline earth metal hydroxide such as calcium hydroxide and barium hydroxide; an alkali metal carbonate such as potassium carbonate and sodium carbonate; ammonia; a tetraalkyl ammonium hydroxide such as tetramethyl ammonium hydroxide and tetraethyl ammonium hydroxide; and an amine such as monomethyl amine, monoethyl amine, monopropyl amine, monobutyl amine, monopentyl amine, dimethyl amine, diethyl amine, trimethyl amine, triethanol amine, and ethylene diamine. Among them, ammonia is most preferable because it can be easily removed from the obtained silicone rubber particle by evaporation. A commercially available aqueous ammonium solution may be used.

In the step (i) of the present method, organotrialkoxysilane is subjected to a hydrolysis and condensation reactions in the presence of water, an alkaline substance and a silicone rubber particle containing therein a liquid, to thereby form a polyorganosilsesquioxane. The resultant polyorganosilsesquioxane is in a state where it adheres to the surface of the silicone rubber particle.

An organotrialkoxysilane is represented, for example, by the formula: $R^5Si(OR^7)_3$, wherein $R^5$ is as described above and $R^7$ is an unsubstituted monovalent hydrocarbon group having 1 to 6 carbon atoms. Examples of $R^7$ include a methyl group, an ethyl group, a propyl group, a butyl group, a pentyl group and a hexyl group. Among these, a methyl group is preferable in view of reactivity. In a case where it is desired to introduce one selected from the units represented by $R^5_2SiO_{2/2}$, $R^5_3SiO_{1/2}$ and $SiO_{4/2}$ into a polyorganosilsesquioxane, at least one compound corresponding to the respective unit and represented by $R^5_2Si(OR^7)_2$, $R^5_3SiOR^7$ or $Si(OR^7)_4$ may be added as a starting material (wherein, $R^5$ and $R^6$ are as defined above). In a case where $R^5Si(OR^7)_3$ and at least one of $R^5_2Si(OR^7)_2$, $R^5_3SiOR^7$ and $Si(OR^7)_4$ are used as starting materials for the polyorganosilsesquioxane, the content of $R^5Si(OR^7)_3$ is preferably 70 mole % or more, or more preferably 80 mole % or more, relative to a total mole of these starting materials. The upper limit may near to 100 mole %.

The amount of the organotrialkoxysilane is such that the content of the polyorganosilsesquioxane is in the range of 1 to 50 parts by mass, preferably 2 to 25 parts by mass, per 100 parts by mass of the silicone rubber particle.

The step of adding the organotrialkoxysilane is conducted preferably under stirring with a usual agitator such as propeller blades and plate blades.

In a case where the organotrialkoxysilane is added after an alkaline substance is added to an aqueous dispersion of water and a silicone rubber particle containing a liquid, the organotrialkoxysilane may be added all at once, but preferably gradually over time. A temperature during this addition is preferably in the range of 0 to 60 degrees C., more preferably 0 to 40 degree C., so that polyorganosilsesquioxane adheres well to the surface of the silicone rubber particle containing a liquid. The stirring is continued even after adding the organotrialkoxysilane until the hydrolysis and condensation reactions of the organotrialkoxysilane completes. In order to complete the hydrolysis and condensation reactions, the reaction may be carried out at room temperature or under heating at 40 to 100 degrees C. Further, if need, the alkaline substance is properly replenished in the reaction mixture.

In the present method, the organotrialkoxysilane may be added before adding an alkaline substance. In this case, it is preferred to first add the organotrialkoxysilane to water. The organotrialkoxysilane may be added to water all at once, or gradually over time. Alternatively, water may be added to the organotrialkoxysilane, or water and the organotrialkoxysilane may be put in a vessel at the same time and mixed. A temperature at which the organotrialkoxysilane is added to water is not limited particularly, and may be, for instance, in the range of from 0 to 100 degrees C. Stirring is continued until at least the organotrialkoxysilane dissolves in water. A small amount of acid may be added in order to promote the hydrolysis reaction.

A silicone rubber particle containing a liquid is added to the solution obtained in the afore-mentioned step and, then, an alkaline substance is added thereto. Then, a condensation reaction of the hydrolysate of the organotrialkoxysilane progresses to thereby form a polyorganosilsesquioxane. The stirring is stopped or made very slow before polyorganosilsesquioxane is produced. If the reaction mixture is flowing at a high speed at the time when polyorganosilsesquioxane is being formed, the polyorganosilsesquioxane does not adhere well to the surface of the silicone rubber particle containing a liquid. A condensation reaction temperature is preferably 0 to 60 degrees C., more preferably 0 to 40 degrees C. When the temperature is in the aforesaid range, the polyorganosilsesquioxane adheres well to the surface of the silicone rubber particle containing a liquid. The reaction solution is preferably left standing or stirred at a very slow speed until polyorganosilsesquioxane is produced, and adheres to the surface of the silicone rubber particle. The time of standing is preferably 10 minutes to 24 hours. After that, an alkaline substance may be added thereto, the reaction mixture may be heated at 40 to 100 degrees C. or usual stirring is further conducted, in order to complete the condensation.

(ii) Step of Removing the Liquid

The present method contains a step of removing the liquid contained in the silicone rubber particle and water by evaporation after polyorganosilsesquioxane adheres to the surface of the silicone rubber particle contained a liquid. In this step, the silicone rubber particle shrinks to form dents on its surface.

The step of removing the liquid contained in the silicone rubber particle may be conducted according to any conventional manner. In a case where the liquid has a high boiling point so that it cannot be removed by volatilization, or where the evaporation conducts at a low temperature, the silicone rubber particle is first washed with a solvent having a low boiling point. The solvent is not limited to any particular one and may be such having a low boiling point among the solvents described above for a liquid to be contained in a silicone rubber particle. One solvent or a mixture of two or more may be used. Before washing, the dispersion may be concentrated by, for instance, thermal dehydration, separation by filtration, centrifugalization or decantation. The dispersion may be dehydrated by heating and, then crushed into powder. Then, a solvent is added to the dispersion, concentrate or powder, and stirred with a usual agitator having propeller blades or flat-plate blades and, then, a solid and a liquid are separated by, for instance, filtration, centrifugalization or decantation. By repeating this step, the liquid contained in the silicone rubber particle is replaced with the solvent having a low boiling point.

The liquid contained in the silicone rubber particle or the solvent exchanged with the liquid in the step of washing, and water may be removed by heating under normal pressure or reduced pressure such as heating the dispersion left standing, heating the dispersion being stirred to flow, spraying the dispersion in hot air stream in a spray dryer to disperse, or using a fluid heating medium. As a pre-treatment before the afore-mentioned step, the dispersion may be concentrated as described above or, if necessary, the dispersion may be washed with water or water-soluble alcohol.

If the silicone composite particles obtained after evaporating and removing the liquid and water is in an agglomerated state, the agglomerate may be crushed by a crusher such as a jet mill, a ball mill and a hammer mill.

EXAMPLES

The present invention will be explained below in further detail with reference to a series of the Examples and the Comparative Examples, though the present invention is in no way limited by these Examples. In the following descriptions, a viscosity is a dynamic viscosity determined at 25 degrees C. with an Ostwald viscometer, and percentage, "%", in a concentration and a content, is by mass.

Example 1

Preparation of an Aqueous Dispersion of a Silicone Rubber Particle Containing Therein Dimethylpolysiloxane In a one-liter glass beaker, put were 264 g of a methyl vinyl polysiloxane which is represented by the following formula (1):

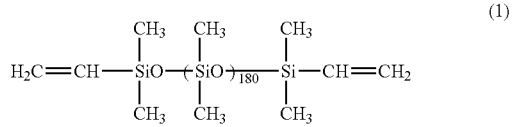

and has a dynamic viscosity of 600 mm$^2$/s; 11 g of a methyl hydrogen polysiloxane which is represented by the following formula (2):

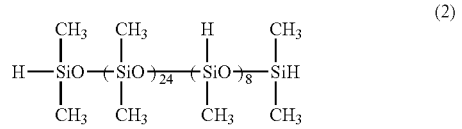

and has a dynamic viscosity of 30 mm$^2$/s, wherein this amount of the methyl hydrogen polysiloxane gives the number of the hydrosilyl groups of 1.18, per olefinic unsaturated group of the methyl vinyl polysiloxane;
and 225 g of a dimethylpolysiloxane which is represented by the following formula (3):

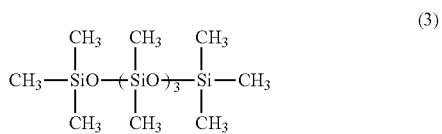

and has a dynamic viscosity of 2 mm$^2$/s and a boiling point of 230 degrees C., wherein this amount of the dimethylpolysiloxane gives 45 parts by mass of the dimethylpolysiloxane, per 100 parts by mass of the silicone rubber particle containing the dimethylpolysiloxane, and stirred with a homomixer at 2,000 rpm to be dissolved each other. Subsequently, 0.8 g of polyoxyethylene lauryl ether having 9 units derived from ethylene oxide, and 100 g of water were added thereto and, then, stirred with a homomixer at 8,000 rpm, whereby an oil-in-water state was obtained and thickening was observed. Then, the stirring was continued for further 15 minutes. Subsequently, 398 g of water was added thereto with stirring at 2,000 rpm to obtain a homogenous white emulsion. This emulsion was taken in a one-liter glass flask equipped with a stirrer having anchor type stirring blades, the temperature thereof was adjusted to 20-25 degrees C., to which then, added with stirring was a solution consisting of 0.5 g of a solution of chloroplatinic acid-olefin complex in toluene, containing 0.5 mass % of platinum, and 1 g of polyoxyethylene lauryl ether having 9 units derived from ethylene oxide. The resulting mixture was stirred for 12 hours at the same temperature to obtain an aqueous dispersion of silicone rubber particles containing therein the dimethylpolysiloxane.

The shape of the silicone rubber particles containing therein the dimethylpolysiloxane in the aqueous dispersion thus obtained was spherical under observation with an optical microscope and the volume-average particle diameter thereof was 12 μm, as determined with a particle size distribution measurement instrument using an electric resistance method, Multisizer 3, manufactured by Beckman Coulter, Inc.

Hardness of the silicone rubber particle was determined according to the following method.

The methyl vinyl polysiloxane represented by the afore-mentioned formula (1), the methyl hydrogen polysiloxane represented by the afore-mentioned formula (2), the dimethylpolysiloxane represented by the afore-mentioned formula (3) and the solution of chloroplatinic acid-olefin complex in toluene, containing 0.5 mass % of platinum, were mixed in the afore-mentioned ratio, poured into an aluminum petri dish up to a depth of 10 mm and allowed to stand at 25 degrees C. for 24 hours. Then, the mixture was heated in a thermostat at 50 degrees C. for one hour to obtain a silicone rubber containing the dimethylpolysiloxane. The silicone rubber thus obtained was removed from the aluminum petri dish and dried in a vaccum dryer at 3×10$^{-3}$ Pa and 100 degrees C. to remove the dimethylpolysiloxane from the silicone rubber to obtain a non-sticky silicone rubber.

Hardness of the silicone rubber was 15, as determined with a durometer A hardness meter.

Preparation of a Silicone Composite Particle

In a two-liter glass flask equipped with a stirrer having anchor type stirring blades, transferred was 300 g of the aqueous dispersion of the silicone rubber particles containing the dimethylpolysiloxane obtained in the afore-mentioned procedures, to which then added were 661 g of water, 19 g of an aqueous 28% ammonium solution and 1 g of an aqueous 40% solution of a dimethyl diallyl ammonium chloride polymer, trade name: ME Polymer H40W, manufactured by Toho Chemical Industry Co., Ltd. At this point of time, a pH of the resulting mixture was 11.8. The temperature of the resulting mixture was adjusted to 5-10 degrees C. and, then, 19 g of methyltrimethoxysilane was gradually added over 20 minutes, wherein this amount would give 11.3 parts by mass of a polymethylsilsesquioxane after the hydrolysis and condensation reactions, per 100 parts by mass of the silicone rubber particles. Then, the stirring was continued for further one hour while maintaining the solution temperature at 5-10 degrees C. Subsequently, the mixture was heated to 55-60 degrees C. and stirred for further one hour while maintaining at this temperature to complete the hydrolysis and condensation reactions of methyltrimethoxysilane.

The aqueous dispersion thus obtained was dehydrated with a press filter to have a water content of approximately 30%. This was transferred to a two-liter glass flask equipped with a stirrer having anchor type stirring blades, 1000 g of water was added thereto, stirred for 30 minutes and, then, dehydration was conducted with a press filter. This was transferred again to a two-liter glass flask equipped with a stirrer having anchor type stirring blades, 1000 g of water was added thereto, stirred for 30 minutes and, then, dehydration was conducted with a press filter. The resultant dehydrated matter was dried in a vacuum dryer at $3 \times 10^{-3}$ Pa and 100 degrees C. to remove the dimethylpolysiloxane contained in the silicone rubber particles and water. The dried matter thus obtained was crushed with a jet mill to obtain fluid silicone composite particles.

The silicone composite particles thus obtained were dispersed in water with a surfactant. The volume-average particle diameter was 11 μm, as determined with a particle size distribution measurement instrument using an electric resistance method, Multisizer 3, manufactured by Beckman Coulter, Inc. Further, it was confirmed under observation with an electron microscope that the silicone rubber particles had plural polyhedral dents on their surfaces. It was further confirmed that particulate polymethylsilsesquioxane having a diameter of about 100 nm adhered on the surface of the silicone particles. FIG. 1 is an electron microscope image of the surface of this silicone composite particle.

Example 2

Preparation of an Aqueous Dispersion of Silicone Rubber Particles Containing Isododecane In a one-liter glass beaker, put were 172 g of a methyl vinyl polysiloxane which is represented by the afore-mentioned formula (1) and has a dynamic viscosity of 600 mm²/s; 7 g of a methyl hydrogen polysiloxane which is represented by the afore-mentioned formula (2) and has a dynamic viscosity of 30 mm²/s, wherein this amount of the methyl hydrogen polysiloxane gives the number of the hydrosilyl groups of 1.15, per olefinic unsaturated group of the methyl vinyl polysiloxane; and 341 g of isododecane, wherein the amount of the isododecane gives 66 parts by mass of the isododecane, per 100 parts by mass of the silicone rubber particles containing the isododecane, and stirred with a homomixer at 2,000 rpm to be dissolved each other. Subsequently, 2 g of polyoxyethylene lauryl ether having 9 units derived from ethylene oxide, and 40 g of water were added thereto and, then, stirred with a homomixer at 8,000 rpm, whereby an oil-in-water state was obtained and thickening was observed. The stirring was continued for further 15 minutes. Subsequently, 437 g of water was added thereto with stirring at 2,000 rpm to obtain a homogenous white emulsion. This emulsion was taken in a one-liter glass flask equipped with a stirrer having anchor type stirring blades, the temperature thereof was adjusted to 20-25 degrees C., to which then added with stirring was a solution consisting of 0.3 g of a solution of chloroplatinic acid-olefin complex in toluene, containing 0.5 mass % of platinum, and 0.5 g of polyoxyethylene lauryl ether having 9 units derived from ethylene oxide. The resulting mixture was stirred for 12 hours at the same temperature to obtain an aqueous dispersion of silicone rubber particles containing isododecane.

The shape of the silicone rubber particles containing isododecane in the aqueous dispersion thus obtained was spherical under observation with an optical microscope and the volume-average particle diameter thereof was 5 μm, as determined with a particle size distribution measurement instrument using an electric resistance method, Multisizer 3, manufactured by Beckman Coulter, Inc.

Hardness of the silicone rubber particle was determined according to the following method.

The methyl vinyl polysiloxane represented by the afore-mentioned formula (1), the methyl hydrogen polysiloxane represented by the afore-mentioned formula (2), isododecane and the solution of chloroplatinic acid-olefin complex in toluene, containing 0.5 mass % of platinum, were mixed in the afore-mentioned ratio, poured into an aluminum petri dish up to a depth of 10 mm and allowed to stand at 25 degrees C. for 24 hours. Then, the mixture was heated in a thermostat at 50 degrees C. for one hour to obtain a silicone rubber containing isododecane. The silicone rubber thus obtained was removed from the aluminum petri dish and dried in a vacuum dryer at $3 \times 10^{-3}$ Pa and 100 degrees C. to remove isododecane from the silicone rubber to obtain a non-sticky silicone rubber.

Hardness of the silicone rubber was 11, as determined with a durometer A hardness meter.

Preparation of a Silicone Composite Particle

In a two-liter glass flask equipped with a stirrer having anchor type stirring blades, transferred was 288 g of the aqueous dispersion of the silicone rubber particles containing isododecane obtained in the afore-mentioned procedures, to which then added were 673 g of water, 19 g of an aqueous 28% ammonium solution and 1 g of an aqueous 40% solution of a dimethyl diallyl ammonium chloride polymer, trade name: ME Polymer H40W, manufactured by Toho Chemical Industry Co., Ltd. At this point of time, a pH of the resulting mixture was 11.8. The temperature of the resulting mixture was adjusted to 5-10 degrees C. and, then, 19 g of methyltrimethoxysilane was gradually added over 20 minutes, wherein this amount would give 18.2 parts by mass of a polymethylsilsesquioxane after hydrolysis and condensation reactions, per 100 parts by mass of the silicone rubber particles. Then, the stirring was continued for further one hour while maintaining the mixture temperature at 5-10 degrees C. Subsequently, the mixture was heated to 55-60 degrees C. and stirred for further one hour while maintaining this temperature, to complete the hydrolysis and condensation reactions of methyltrimethoxysilane.

The aqueous dispersion thus obtained was dehydrated with a press filter to have a water content of approximately 30%. This was transferred to a two-liter glass flask equipped with a stirrer having anchor type stirring blades, 1000 g of water was added thereto, stirred for 30 minutes and, then, dehydrated with a press filter. This was transferred again to a two-liter glass flask equipped with a stirrer having anchor type stirring blades, 1000 g of water was added thereto, stirred for 30 minutes and, then, dehydrated with a press filter. The resultant dehydrated matter was dried in a vacuum dryer at $3 \times 10^{-3}$ Pa and 100 degrees C. to remove isododecane remaining in the silicone rubber particles and water. The dried matter thus obtained was crushed with a jet mill to obtain fluid silicone composite particles.

Figure 2:
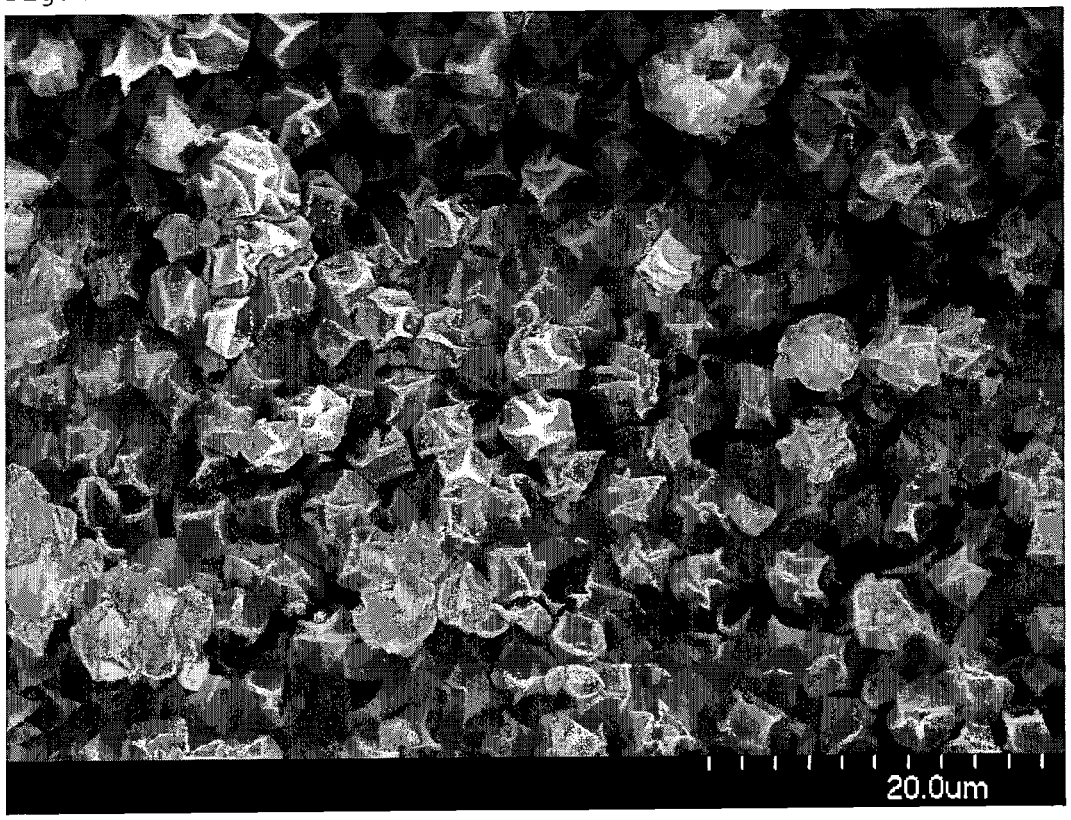
FIG. 2 is an electron microscope image of a surface of the silicone composite particle obtained in Example 2.

The silicone composite particles thus obtained were dispersed in water with a surfactant. The volume-average particle diameter was 3 μm, as determined with a particle size distribution measurement instrument using an electric resistance method, Multisizer 3, manufactured by Beckman Coulter, Inc. Further, it was confirmed under observation with an electron microscope that the silicone rubber particles had about 4 to 10 tetrahedral or pentahedral dents on the surface of each particle. It was further confirmed that particulate polymethylsilsesquioxane having a diameter of about 80 nm adhered on the surfaces. FIG. 2 is an electron microscope image of the surface of this silicone composite particle.

Comparative Example 1

Preparation of an Aqueous Dispersion of Silicone Rubber Particles Containing No Liquid In a one-liter glass beaker, put were 442 g of a methyl vinyl polysiloxane which is represented by the afore-mentioned formula (1) and has a dynamic viscosity of 600 mm²/s and 58 g of a methyl hydrogen polysiloxane which is represented by the following formula (4):

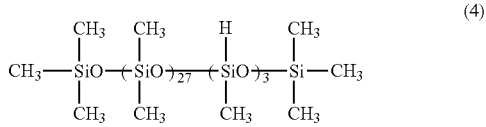

and has a dynamic viscosity of 28 mm²/s, wherein the amount of methyl hydrogen polysiloxane gives the number of the hydrosilyl groups of 1.14, per olefinic unsaturated group of the methyl vinyl polysiloxane, and stirred with a homomixer at 2,000 rpm to be dissolved each other. Subsequently, 0.8 g of polyoxyethylene lauryl ether having 9 units derived from ethylene oxide and 100 g of water were added thereto and, then, stirred with a homomixer at 8,000 rpm, whereby an oil-in-water state was obtained and thickening was observed. Then, the stirring was continued for further 15 minutes. Subsequently, 398 g of water was added thereto with stirring at 2,000 rpm to obtain a homogenous white emulsion. This emulsion was taken in a one-liter glass flask equipped with a stirrer having anchor type stirring blades, and the temperature thereof was adjusted to 20-25 degrees C., to which, then, added with stirring was a solution consisting of 0.8 g of a solution of chloroplatinic acid-olefin complex in toluene, containing 0.5 mass % of platinum, and 1 g of polyoxyethylene lauryl ether having 9 units derived from ethylene oxide. The resulting mixture was stirred for 12 hours at the same temperature to obtain an aqueous dispersion of silicone rubber particles which did not contain any liquid.

The shape of the silicone rubber particles in the aqueous dispersion thus obtained was spherical under observation with an optical microscope and the volume-average particle diameter thereof was 13 μm, as determined with a particle size distribution measurement instrument using an electric resistance method, Multisizer 3, manufactured by Beckman Coulter, Inc.

Hardness of the silicone rubber particle was determined according to the following method.

The methyl vinyl polysiloxane represented by the afore-mentioned formula (1), the methyl hydrogen polysiloxane represented by the afore-mentioned formula (4) and a solution of chloroplatinic acid-olefin complex in toluene, containing 0.5 mass % of platinum, were mixed in the afore-mentioned ratio, poured into an aluminum petri dish up to a depth of 10 mm and allowed to stand at 25 degrees C. for 24 hours. Then, the mixture was heated in a thermostat at 50 degrees C. for one hour to obtain a non-sticky silicone rubber. Hardness of the silicone rubber was 13, as determined with a durometer A hardness meter.

Preparation of a Silicone Composite Particle

In a two-liter glass flask equipped with a stirrer having anchor type stirring blades, transferred was 300 g of the aqueous dispersion of the silicone rubber particles obtained in the afore-mentioned procedures, to which then added were 661 g of water and 19 g of an aqueous 28% ammonium solution. At this point of time, a pH of the resulting mixture was 11.8. The temperature of the resulting mixture was adjusted to 5-10 degrees C. and, then, 20 g of methyltrimethoxysilane was gradually added over 20 minutes, wherein this amount was would give 6.6 parts by mass of a polymethylsilsesquioxane after the hydrolysis and condensation reactions, per 100 parts by mass of the silicone rubber mixture. Then, the stirring was continued for further one hour while maintaining the mixture temperature at 5-10 degrees C. Subsequently, the mixture was heated to 55-60 degrees C. and stirred for further one hour while maintaining this temperature, to complete the hydrolysis and condensation reactions of methyltrimethoxysilane.

The aqueous dispersion thus obtained was dehydrated with a press filter to a water content of approximately 30%. This was transferred to a two-liter glass flask equipped with a stirrer having anchor type stirring blades, 1000 g of water was added thereto, stirred for 30 minutes and, then, dehydrated was conducted with a press filter. This was transferred again to a two-liter glass flask equipped with a stirrer having anchor type stirring blades, 1000 g of water was added thereto, stirred for 30 minutes and, then, dehydrated with a press filter. The resultant dehydrated matter was dried in a vaccum dryer at 105 degrees C. to remove water. The dried matter thus obtained was crushed with a jet mill to obtain fluid silicone composite particles.

Figure 3:
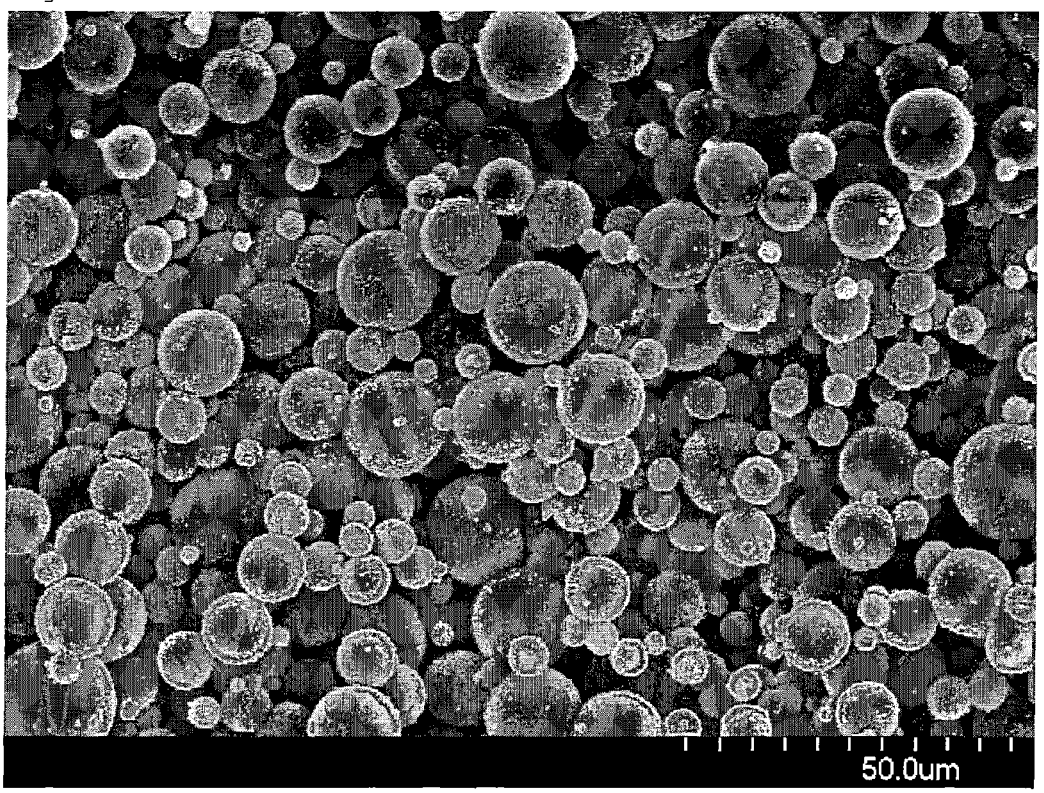
FIG. 3 is an electron microscope image of a surface of the silicone composite particle obtained in Comparative Example 1.

The silicone composite particles thus obtained were dispersed in water with a surfactant. The volume-average particle diameter was 13 μm, as determined with a particle size distribution measurement instrument using an electric resistance method, Multisizer 3, manufactured by Beckman Coulter, Inc. Further, it was confirmed under observation with an electron microscope that the surface of the silicone rubber particles was covered with particulate polymethylsilsesquioxane having a diameter of about 100 nm, but had no dent. FIG. 3 is an electron microscope image of the surface of this silicone composite particle.

Comparative Example 2

The aqueous dispersion of the silicone rubber particles obtained in Example 1, which contained dimethylpolysiloxane, was dried with a spray dryer to remove water and obtain powder. The resultant powder was dried in a vacuum dryer at 3×10⁻³ Pa and 100 degrees C. to remove dimethylpolysiloxane from the silicone rubber particles to obtain silicone rubber particles. It was confirmed under observation with an electron microscope that the silicone rubber particles were spherical particles having no dent.

Comparative Example 3

Preparation of an Aqueous Dispersion of a Silicone Rubber Particle Containing Dimethylpolysiloxane and Having High Hardness In a one-liter glass beaker, put were 360 g of a methyl vinyl polysiloxane which is represented by the following formula (5):

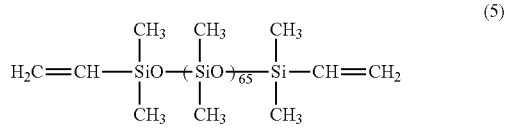

and has a dynamic viscosity of 100 mm$^2$/s; 40 g of a methyl hydrogen polysiloxane which is represented by the afore-mentioned formula (2) and has a dynamic viscosity of 30 mm$^2$/s, wherein the amount of the methyl hydrogen polysiloxane gives the number of the hydrosilyl groups of 1.16, per olefinic unsaturated group of the methyl vinyl polysiloxane; and 100 g of a dimethylpolysiloxane which is represented by the afore-mentioned formula (3) and has a dynamic viscosity of 2 mm$^2$/s and a boiling point of 230 degrees C., wherein this amount of the dimethylpolysiloxane gives 20 parts by mass of the dimethylpolysiloxane, per 100 parts by mass of silicone rubber particles containing the dimethylpolysiloxane, and stirred with a homomixer at 2,000 rpm to be dissolved each other. Subsequently, 0.8 g of polyoxyethylene lauryl ether having 9 units derived from ethylene oxide and 100 g of water were added thereto and, then, stirred with a homomixer at 8,000 rpm, whereby an oil-in-water state was obtained and thickening was observed. Then, the stirring was continued for further 15 minutes. Subsequently, 398 g of water was added thereto with stirring at 2,000 rpm to obtain a homogenous white emulsion. This emulsion was taken in a one-liter glass flask equipped with a stirrer having anchor type stirring blades, and the temperature thereof was adjusted to 20-25 degrees C., to which then, added with stirring was a solution consisting of 0.8 g of a solution of chloroplatinic acid-olefin complex in toluene, containing 0.5 mass % of platinum, and 1 g of polyoxyethylene lauryl ether having 9 units derived from ethylene oxide. The resulting mixture was stirred for 12 hours at the same temperature to obtain an aqueous dispersion of silicone rubber particles containing dimethylpolysiloxane.

The shape of the silicone rubber particles in the aqueous dispersion thus obtained was spherical under observation with an optical microscope and the volume-average particle diameter thereof was 13 μm, as determined with a particle size distribution measurement instrument using an electric resistance method, Multisizer 3, manufactured by Beckman Coulter, Inc.

Hardness of the silicone rubber particle was determined according to the following method.

The methyl vinyl polysiloxane represented by the afore-mentioned formula (5), the methyl hydrogen polysiloxane represented by the afore-mentioned formula (2), the dimethylpolysiloxane represented by the afore-mentioned formula (3) and a solution of chloroplatinic acid-olefin complex in toluene, containing 0.5 mass % of platinum, were mixed in the afore-mentioned ratio, poured into an aluminum petri dish up to a depth of 10 mm and allowed to stand at 25 degrees C. for 24 hours. Then, the mixture was heated in a thermostat at 50 degrees C. for one hour to obtain a silicone rubber containing the dimethylpolysiloxane. The silicone rubber containing the dimethylpolysiloxane thus obtained was removed from the aluminum petri dish and dried in a vacuum dryer at 3×10$^{-3}$ Pa and 100 degrees C. to remove the dimethylpolysiloxane from the silicone rubber and obtain non-sticky silicone rubber.

Hardness of the silicone rubber was 38, as determined with a durometer A hardness meter.

Preparation of a Silicone Composite Particle

In a two-liter glass flask equipped with a stirrer having anchor type stirring blades, transferred was 300 g of the aqueous dispersion of the silicone rubber particles containing the dimethylpolysiloxane obtained in the afore-mentioned procedures, to which then added were 661 g of water, 19 g of an aqueous 28% ammonium solution, and 1 g of an aqueous 40% solution of dimethyl diallyl ammonium chloride polymer, trade name: ME Polymer H40W, manufactured by Toho Chemical Industry Co., Ltd. At this point of time, a pH of the resulting mixture was 11.8. The temperature of the resulting mixture was adjusted to 5-10 degrees C. and, then, 19 g of methyltrimethoxysilane was gradually added over 20 minutes, wherein this amount would give 7.8 parts by mass of the polymethylsilsesquioxane after the hydrolysis and condensation reactions, per 100 parts by mass of the silicone rubber particle. Then, the stirring was continued for further one hour while maintaining the mixture temperature at 5-10 degrees C. Subsequently, the mixture was heated to 55-60 degrees C. and stirred for further one hour while maintaining this temperature, to complete the hydrolysis and condensation reactions of methyltrimethoxysilane.

The aqueous dispersion thus obtained was dehydrated with a press filter to a water content of approximately 30%. This was transferred to a two-liter glass flask equipped with a stirrer having anchor type stirring blades, 1000 g of water was added thereto, stirred for 30 minutes and, then, dehydrated with a press filter. This was transferred again to a two-liter glass flask equipped with a stirrer having anchor type stirring blades, 1000 g of water was added thereto, stirred for 30 minutes and, then, dehydrated with a press filter. The resultant dehydrated matter was dried in a vacuum dryer at 3×10$^{-3}$ Pa and 100 degrees C. to remove the dimethylpolysiloxane remaining in the silicone rubber particles and water. The dried matter thus obtained was crushed with a jet mill to obtain fluid silicone composite particles.

The silicone composite particles thus obtained were dispersed in water with a surfactant. The volume-average particle diameter was 12 μm, as determined with a particle size distribution measurement instrument using an electric resistance method, Multisizer 3, manufactured by Beckman Coulter, Inc. Further, it was confirmed under observation with an electron microscope that the surface of the silicone rubber particles was covered with particulate polymethylsilsesquioxane having a diameter of about 80 nm and that the silicone composite particles were spherical with no dent.

INDUSTRIAL APPLICABILITY

The present silicone composite particle is expected to provide a higher light scattering effect and, therefore, is expected to be useful for cosmetics.

The invention claimed is:
1. A method for preparing a silicone composite particle composed of a silicone rubber particle and a polyorganosilsesquioxane, wherein the silicone rubber particle has plural dents on its surface and said polyorganosilsesquioxane adheres to the surface of the silicone rubber particle, wherein the method comprises steps of provaiding a silicone rubber particle containing therein a liquid which is one or more selected from aliphatic hydrocarbons, aromatic hydrocarbons, alcohols, halogenated hydrocarbons, esters, ethers, ketones, and organopolysiloxanes;

subjecting organotrialkoxysilane to hydrolysis and condensation reactions in the presence of water, an alkaline substance, and the silicone rubber particle containing therein said liquid to produce polyorganosilsesquioxane on the surface of the silicone rubber particle, to thereby have a resultant polyorganosilsesquioxane adhered to the surface of the silicone rubber particle; and subsequently removing said liquid and water.

2. The method according to claim 1, wherein said liquid is dissolved in a curable liquid silicone composition to form a solution, adding a surfactant and water to the obtained solution, emulsifying them, and curing the curable liquid silicone composition in the presence of a catalyst to thereby have said liquid contained in a resultant silicone rubber particle.

3. The method according to claim 1, wherein an amount of the liquid is 5 to 80 parts by mass, per 100 parts by mass of the silicone rubber particle containing therein the liquid.

* * * * *